US008216434B2

United States Patent
Hsiai et al.

(10) Patent No.: US 8,216,434 B2
(45) Date of Patent: Jul. 10, 2012

(54) MEMS VASCULAR SENSOR

(75) Inventors: Tzung K. Hsiai, Santa Monica, CA (US); Gopikrishnan Soundararajan, Alisa Viejo, CA (US); Eun Sok Kim, Rancho Palos Verdes, CA (US); Hongyu Yu, Mesa, AZ (US); Mahsa Rouhanizadeh, Newport Beach, CA (US); Christina Tiantian Lin, Santa Rosa, CA (US)

(73) Assignee: University of Southern California, Los Angeles, CA (US)

(*) Notice: Subject to any disclaimer, the term of this patent is extended or adjusted under 35 U.S.C. 154(b) by 1069 days.

(21) Appl. No.: 12/041,577

(22) Filed: Mar. 3, 2008

(65) Prior Publication Data

US 2008/0210543 A1 Sep. 4, 2008

Related U.S. Application Data

(62) Division of application No. 11/196,849, filed on Aug. 4, 2005, now Pat. No. 7,367,237.

(60) Provisional application No. 60/601,101, filed on Aug. 12, 2004.

(51) Int. Cl.
*C23C 14/34* (2006.01)

(52) U.S. Cl. ............ 204/192.15; 204/192.17; 438/50; 438/54; 438/694; 438/706; 438/712; 438/724; 438/753; 438/757; 216/2; 216/58; 216/66; 216/99

(58) Field of Classification Search ............ 204/192.15, 204/192.17; 216/2, 58, 66, 99; 438/50, 54, 438/694, 706, 712, 724, 753, 757
See application file for complete search history.

(56) References Cited

U.S. PATENT DOCUMENTS

| 5,242,863 A | 9/1993 | Xiang-Zheng et al. |
| 5,291,781 A | 3/1994 | Nagata et al. |
| 5,511,428 A * | 4/1996 | Goldberg et al. ............... 73/777 |
| 5,883,310 A | 3/1999 | Ho et al. |
| 6,044,705 A | 4/2000 | Neukermans et al. |
| 6,071,819 A | 6/2000 | Tai et al. |
| 6,341,532 B1 | 1/2002 | Xu et al. |
| 6,408,698 B1 | 6/2002 | Brereton et al. |

(Continued)

OTHER PUBLICATIONS

Rouhnizadeh M., Soundararajan G., Ascara D., Lo R., Browand F., Hsiai T.K., MEMS sensors to resolve spatial variations in shear stress in a 3-D blood vessel bifurcation model. IEEE Sensors Journal, Feb. 2006, pp. 78-88, vol. 6, No. 10, Piscataway, NJ.

(Continued)

*Primary Examiner* — Rodney McDonald
(74) *Attorney, Agent, or Firm* — McDermott Will & Emery LLP

(57) ABSTRACT

A micromachined sensor for measuring vascular parameters, such as fluid shear stress, includes a substrate having a front-side surface, and a backside surface opposite the front-side surface. The sensor includes a diaphragm overlying a cavity etched within the substrate, and a heat sensing element disposed on the front-side surface of the substrate and on top of the cavity and the diaphragm. The heat sensing element is electrically couplable to electrode leads formed on the backside surface of the substrate. The sensor includes an electronic system connected to the backside surface and configured to measure a change in heat convection from the sensing element to surrounding fluid when the sensing element is heated by applying an electric current thereto, and further configured to derive from the change in heat convection vascular parameters such as the shear stress of fluid flowing past the sensing element.

6 Claims, 6 Drawing Sheets

U.S. PATENT DOCUMENTS

| | | |
|---|---|---|
| 6,825,539 B2 | 11/2004 | Tai et al. |
| 6,852,216 B2 | 2/2005 | Moscaritolo et al. |
| 6,855,249 B2 | 2/2005 | Moscaritolo |
| 6,877,385 B2 | 4/2005 | Fang et al. |
| 6,901,794 B2 | 6/2005 | Zobel et al. |
| 2004/0093932 A1 | 5/2004 | Hajduk et al. |
| 2006/0107752 A1 | 5/2006 | Kotovsky |

OTHER PUBLICATIONS

Soundararajan G., Rouhnizadeh M., Yu H., Demaio L., Kim E.S., and Hsiai T.K., MEMS Shear stress sensors for microcirculation, Sensors and Actuators A: Physical, 2005, pp. 25-32, vol. 118, No. 1, Elsevier B.V., New York.

Soundararajan G., Hsiai T., Microsensors to characterize shear stress regulating MCP-1 expression in vessel bifurcations, Annals of Biomedical Engineering, Feb. 2004, vol. 32, No. 2, pp. 189-201 San Francisco.

Soundararajan G., Rouhnizadeh M., Demaio L., and Hsiai T.K., MEMS Shear stress sensors for cardiovascular diagnostics, Proceedings of the 26th Annual International Conference of the IEEE EMBS, Sep. 1-5, 2004, pp. 2420-2423, San Francisco.

Soundararajan G., Rouhnizadeh M., Yu, H., E.S. Kim, and Hsiai T.K., Micro sensors to detect shear stress on vascular cells, 11th Foresight Conference on Molecular Nanotechnology, 2003, San Francisco.

Rouhnizadeh M., Demaio L., Ascara D., Hsiai, T., Spatial variations in shear stress at low reynolds numbers. Annals of Biomedical Engineering, Oct. 2005, vol. 33, No. 10, pp. 1360-1374. Springer, New York.

* cited by examiner

Silicon(110)
Silicon nitride(112)
Silicon oxide(170)
Aluminum(160)
Phosphorous-doped polysilicon(123)

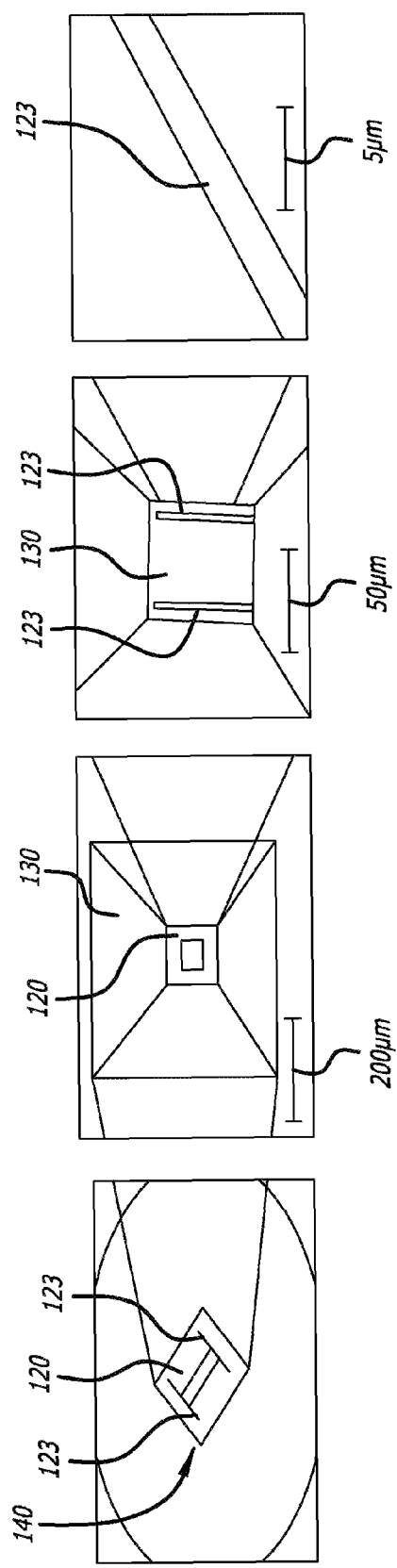

MEMS VASCULAR SENSOR

CROSS REFERENCE TO RELATED APPLICATIONS

This application is a divisional application of U.S. patent application Ser. No. 11/196,849, filed Aug. 4, 2005, entitled "MEMS Vascular Sensor," now U.S. Pat. No. 7,367,237 B2, issued May 6, 2008, which claims the benefit of priority under 35 U.S.C. §119(e) from co-pending, commonly owned U.S. provisional patent application Ser. No. 60/601,101, filed on Aug. 12, 2004, entitled "Backside Wire Bonding For Micro Circuitry." The entire content of both of these applications is incorporated herein by reference.

GOVERNMENT'S INTEREST IN APPLICATION

This invention was made with government support under Grant No. HL068689-01, awarded by the National Institutes for Health. The government has certain rights in the invention.

BACKGROUND

Coronary artery disease may be one of the leading causes of morbidity and mortality in the industrialized nations. Vascular parameters, in particular shear stress acting on blood vessel walls, may play an important role in regulating the development of atherosclerosis, because shear stress may intimately modulate the biological activities of vascular endothelial cells (ECs), which line the inner lumen of blood vessels. Shear stress has been directly correlated with the distribution of focal atherosclerotic lesions in the arterial wall. Also, there is growing evidence that disturbed blood flow, or decreased wall shear stress associated with flow separation, favors the formation of arteriosclerosis.

Measurement of shear stress is thus important for the pathogenesis of coronary artery diseases. In addition, shear stress measurement may be important in order to study the durability of prosthetic valves, as well as to monitor platelet aggregation in cardiopulmonary bypass machines, and in artificial heart and left ventricular assist devices (LVADs). Diagnostically, luminal shear stress measurement may predict the development of atherosclerotic plaque in patients at risk for acute coronary syndrome. Further, luminal shear stress measurement may provide clinical information that can predict recurrent plaque formations in patients who have undergone intravascular stent deployment or bypass graft.

Measurement of wall shear stress, in particular near-wall shear stress, remains an engineering challenge, however. The wall shear stress as obtained from a laser Doppler velocimeter or a particle image velocimeter, may have an increased noise level, due to the reflection from the wall. Another challenge is the application of in-situ devices such as heated wires, which have to be employed close to the vessel wall to measure shear stress. Typically, the vessel wall may act as a potential heat sink, diverting the direction of convective heat transfer from the hot wires so that heat is conveyed to the vessel wall, instead of to the working fluid or blood. This causes a decrease in the sensitivity of the measurements.

Measuring temporal and spatial variations in shear stress, both of which have been implicated in the pathogenesis of atherosclerosis, is especially challenging. Micromachined MEMS (micro-electro-mechanical) sensors may provide possibilities for in-situ shear stress measurement, and for overcoming difficulties in measuring temporal and spatial variations in shear stress. Operating the MEMS sensors in a liquid environment, as may be necessary in many biomedical applications, may affect the sensitivity of the MEMS sensors. For example, MEMS sensors that are driven by front-side wire bonding may require insulation using sealants, which however may undergo expansion after prolonged exposure to the fluidic environment. Also, in MEMS sensors for which wire bonding is established on the front side, the elevation of microcircuitry on the same side of sensing element may disturb the local flow milieu, thus negatively affecting the precision of the shear stress measurement.

For these reasons, there is a need for improved methods and systems for precisely measuring real-time shear stress in microfluidic channels and microcirculation, as well as in large-scale arterial circulation.

SUMMARY

A micromachined sensor for measuring fluid shear stress may include a substrate having a front-side surface, and a backside surface opposite the front-side surface. The sensor may include a diaphragm overlying a cavity etched within the substrate. The sensor may include a heat sensing element disposed on the front-side surface of the substrate and on top of the cavity and the diaphragm. The heat sensing element may be electrically couplable to electrode leads formed on the backside surface of the substrate. The sensor may include an electronic system connected to the backside surface and configured to measure a change in heat convection from the sensing element to surrounding fluid when the sensing element is heated by applying an electric current thereto, and further configured to derive from the change in heat convection a shear stress of the surrounding fluid that flows past the sensing element.

A method of fabricating a micromachined shear stress sensor may include depositing a layer of silicon nitride on a substrate having a front-side surface and a backside surface. The method may include etching the substrate to form a cavity having an overlying diaphragm, and performing reactive ion etching on the diaphragm to create a plurality of access slits on the diaphragm.

The method may include conformally depositing a layer of polysilicon on the substrate, then doping the polysilicon layer with phosphorus. The method may include sputtering a layer of aluminum onto the backside surface of the substrate, and patterning the aluminum layer to form a plurality of electrode leads. The method may further include patterning the polysilicon layer on the front-side surface of the substrate to form a strip heat sensing element. The method may further include connecting a plurality of wire bonds between the sensing element on the front-side surface and the electrode leads on the backside surface, by passing the wire bonds through the access slits on the diaphragm.

A method of measuring shear stress on a blood vessel wall may include introducing a backside wire-bonded MEMS sensor into a desired location in a flow field of blood flowing though a blood vessel. The MEMS sensor may include a heat sensing element disposed on a front-side surface of a substrate, the heat sensing element interfacing the flowing blood and coupled to electrode leads formed on a backside surface of the substrate opposite the front-side surface. The method may include applying an electrical current to the sensing element from a driving circuit coupled to the backside surface. The method may further include measuring a change in heat convection from the sensing element to surrounding blood fluid, by measuring a voltage that needs to be applied across the heat sensing element in order to maintain the sensing element at a substantially constant temperature. The method may further include deriving the shear stress at the desired location from the measured change in heat convection.

An apparatus for measuring shear stress from arterial circulation may include a flexible catheter, and a MEMS sensor attached to the distal end of the flexible catheter. The MEMS sensor may include a heat sensing element disposed on a front-side surface of a substrate and interfacing a flow of blood through a vessel. The heat sensing element may be thermally insulated from the substrate through a cavity etched in the substrate. The heat sensing element may be electrically coupled to a backside surface of the substrate by bond wires.

A driving circuit may be electrically coupled to the backside surface of the substrate and configured to drive the MEMS sensor. The driving circuit may be configured to apply an electric current through the sensing element to resistively heat the sensing element. The driving circuit may be further configured to apply a voltage across the sensing element necessary to maintain the sensing element at a substantially constant temperature. The apparatus may further include a processing system configured to determine from the voltage applied by the driving circuit a change in heat convection from the sensing element to blood surrounding the sensing element, and deriving from the change in heat convection a shear stress of blood flowing through the vessel past the sensing element.

A micromachined sensor for measuring one or more vascular parameters may include a substrate having a front-side surface, and a backside surface opposite the front-side surface. The sensor may include a diaphragm overlying a cavity etched within the substrate. The sensor may include a heat sensing element disposed on the front-side surface of the substrate and on top of the cavity and the diaphragm. The heat sensing element may be electrically couplable to electrode leads formed on the backside surface of the substrate. The sensor may include an electronic system connected to the backside surface and configured to measure a change in heat convection from the sensing element to surrounding fluid when the sensing element is heated by applying an electric current thereto, and further configured to derive the vascular parameters from the measured change in heat convection.

BRIEF DESCRIPTION OF THE DRAWINGS

FIGS. 4A-4D illustrate SEM photos of the MEMS shear stress sensor.

DETAILED DESCRIPTION

A system and method are disclosed for measuring fluid shear stress with a MEMS shear stress sensor, and for fabricating the MEMS sensor. The MEMS sensor may be backside wire bonded, and may operate based on basic heat transfer principles. The backside wire bonding may insulate the micro-circuitry in the MEMS sensor from the fluid. The MEMS sensor may include an etched cavity that may improve the sensitivity of the sensor by minimizing heat conductance loss from the heat sensing component of the sensor.

Figure 1:
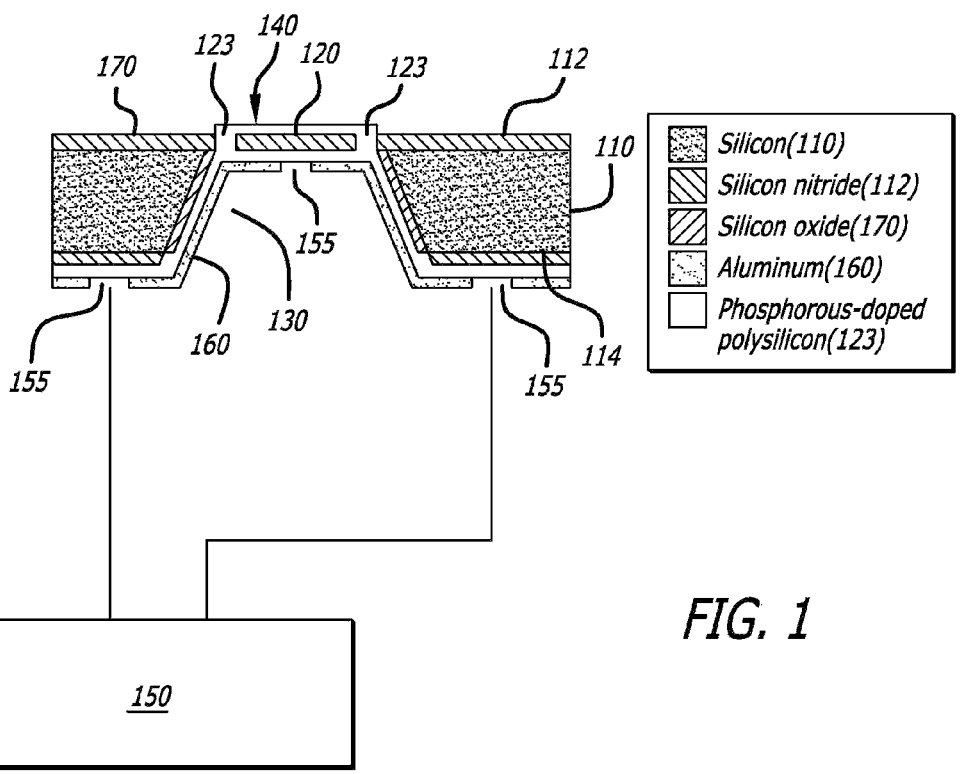
FIG. 1 is a schematic diagram illustrating a MEMS shear stress sensor.

FIG. 1 is an overall schematic diagram of a MEMS shear stress sensor 100, constructed in accordance with one embodiment of the methods and systems described in this disclosure. In overview, the MEMS sensor 100 may include: a substrate 110 having a front-side surface 112 and a backside surface 114 opposite the front-side surface; a diaphragm 120 overlying a cavity 130 etched within the substrate 110; a heat sensing element 140 disposed on the front-side 112 of the substrate 110 and wire-bonded to the backside surface 114; and an electronic system 150 that includes electronic circuitry for making the measurements and computations necessary to derive the desired shear stress. Using backside wire bonding, the sensor 100 may be constructed so that only the sensing element 140, but not the electronic circuitry, interfaces the flowing fluid. The MEMS sensor 100 in one embodiment may be comparable in size to an elongated vascular endothelial cell (EC). For example, the MEMS sensor 100 may have a size of about 1000×875×850 µm.

After an electric current is applied through the sensing element 140, a change in heat convection from the resistively heated sensing element 140 to the flowing fluid is measured, from which a value for shear stress is inferred using basic heat transfer equations described in further detail below. The electronic system 150 may thus be configured to measure a change in heat convection from the sensing element 140 to the surrounding fluid when the sensing element 140 is heated by applying an electric current thereto. The electronic system 150 may thus be further configured to derive from the measured change in heat convection a shear stress of the fluid that interfaces and flows past the sensing element 140.

Changes in heat convection may be measured by determining the changes in voltage across the sensing element. The changes in voltage may be calibrated to the shear stress, as described further below and illustrated in FIG. 7B. Further, these changes in voltage may be calibrated to measurements of vascular parameters other than shear stress, including but not limited to pressure, flow rate, and temperature.

The heat sensing element 140 may be disposed on the front-side surface 112 of the substrate 110, and on top of the cavity 130 and the diaphragm 120. A number of electrode leads 155 may be formed on the backside surface 114 of the substrate 110. The heat sensing element 140 on the front-side surface 112 may be configured to be electrically coupled by bond wires to the electrode leads 155 on the backside surface 114 of the substrate 110, which in turn is coupled to the electronic micro-circuitry in the electronic system 150. In this way, the sensor 100 is backside wire bonded, and only the heat sensing element 140, but not the micro-circuitry, is exposed to the flowing blood fluid.

In one embodiment, the sensing element 140 may be a polysilicon strip, uniformly doped with phosphorus, and may have a length of about 80 µm, a width of about 2 µm, and a depth of about 0.5 μm. The resistance of the sensing element 140 may be adjusted by changing the doping concentration. In one embodiment, the doping may be performed at a concentration of about $10^{16}$ cm$^2$, which may result in a sheet resistance of 32 Ω/cm$^2$, and a resistance value of 2.5 kΩ at room temperature. In general, the resistance of the sensing element 140 made of polysilicon doped with phosphorus may range from about 1 kΩ to 5 kΩ, which is much higher than the resistances typically found in conventional metal sensors (about 5Ω to about 50Ω). This may greatly increase the sensitivity of MEMS sensors.

As seen in FIG. 1, the sensing element 140 may be disposed on the diaphragm 120 above the cavity 130. The cavity 130 may be a formed by anisotropic wet etching by KOH. The cavity 130 provides effective thermal isolation between the sensing element 140 and the substrate 110, by minimizing the heat conduction from the diaphragm 120 to the substrate 110, and thus optimizing unidirectional convective heat transfer from the sensing element 140 to the flowing fluid. The KOH-etched cavity eliminates the need for additional masks and fabrication steps, which were needed in order to obtain thermal isolation in front-side wire bonded MEMS sensors in which the sensing elements are deposited on a surface micromachining-created vacuum cavity on the front side.

The diaphragm 120 resulting from the KOH-etched cavity 130 may improve the sensitivity of the sensor 100 by directing the convective heat transfer from the phosphorous-doped sensing element 140 to the biological fluids, and minimizing heat transfer to the silicon substrate 110 by conductive heat loss. The diaphragm 120 may be formed by a layer of silicon nitride deposited on the substrate, for example using low pressure chemical vapor deposition (LPCVD), then etching the cavity 130. This may be followed by thermal oxidation, which may create a layer 170 of silicon oxide, as described in further detail in conjunction with FIGS. 3A-3C.

The diaphragm 120 may include a pair of access slits 123, which may be formed by reactive ion etching (RIE), and which may permit passage of bond wires therethrough so that the heat sensing element 140 can be connected to the electrode leads 155 on the backside surface 114 of the substrate 110 through the bond wires. The diaphragm 120 thus enables backside wire bonding for the MEMS sensor 100, by establishing electric contact between the aluminum metallization on the backside surface 114 and the sensing element 140 through the RIE-etched slits 123. The electrode leads 155 on the backside surface 114, which allow bond wires to connect to the phosphorous-doped polysilicon sensing element on the front side surface, may be formed by thermal evaporation of a layer of aluminum 160.

Figure 2A:
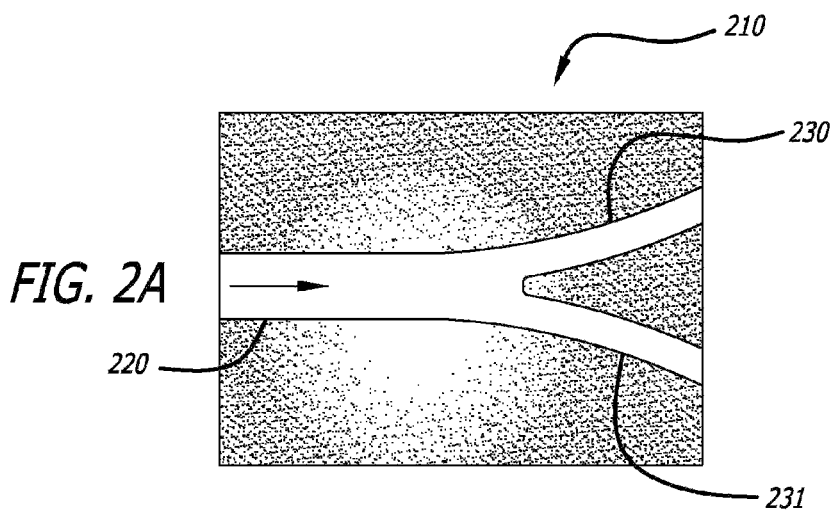
FIG. 2A illustrates an exemplary 3-D model of an arterial bifurcation.
Figure 2B:
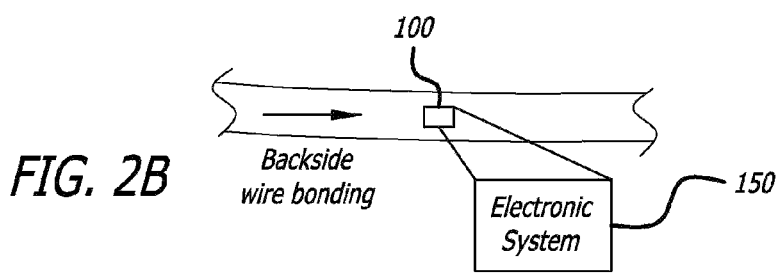
FIG. 2B illustrates a backside wire bonded MEMS sensor mounted on an inlet branch of an arterial bifurcation.

The MEMS sensor 100 may be placed at a desired location along the blood vessel, for example near an arterial bifurcation. For this purpose, a flexible catheter (not shown) may be used, for example, and the MEMS sensor 100 may be attached to a distal end of the flexible catheter. Heart disease, i.e. atherosclerosis, preferentially develops at arterial branching points or bifurcations. FIG. 2A illustrates an exemplary 3-D model of an arterial bifurcation 210, showing the relation between the inlet branch 220 and two symmetric outlet branches 230 and 231. FIG. 2B illustrates a backside wire bonded MEMS sensor 100 mounted on an inlet branch of an arterial bifurcation. As illustrated in FIG. 2B, backside wire bonding may shield the sensor electronic circuitry (connected to the electrode leads on the backside surface of the sensor) from being exposed to biological fluids. This may allow for precise shear stress measurement without causing flow disturbance from the wire bonding.

Figure 3A:
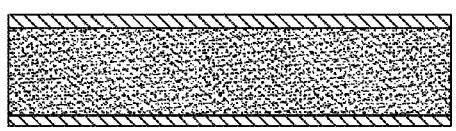
FIGS. 3A-3I schematically illustrate an exemplary fabrication process of the MEMS shear stress sensor shown in FIG. 1.
Figure 3B:
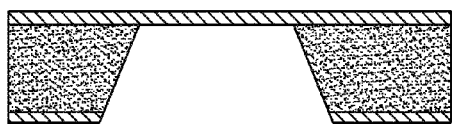
Figure 3F:
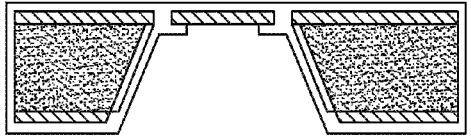
Figure 3C:
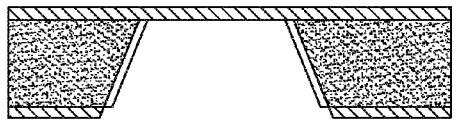

FIGS. 3A-3I schematically illustrate an exemplary fabrication process of the MEMS shear stress sensor shown in FIG. 1. As shown in FIG. 3A, as an initial act in the fabrication of the MEMS sensor 100, silicon nitride may be uniformly deposited on the substrate 110, by LPCVD, at about 0.4 μm in thickness. As shown in FIG. 3B, a cavity may then be created by anisotropic wet etching using KOH. In one embodiment, the wet etching may be performed for about 400 minutes at about 44% concentration. In the illustrated embodiment, the resulting area of the silicon nitride diaphragm 120 may be measured at about 595.3×595.3 μm in width. FIG. 3C illustrates the formation of a SiO$_2$ layer by thermal oxidation. Thermal oxidation may be performed at about 1050 degrees Celsius, for about 30 minutes. The SiO$_2$ layer may have a thickness of about 162.5 nm. The thickness of SiO$_2$ layer may be made to be greater than 100 nm, in order to prevent pinhole formation in the SiO$_2$.

Figure 3G:
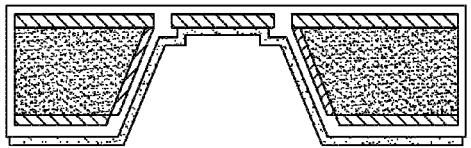
Figure 3D:
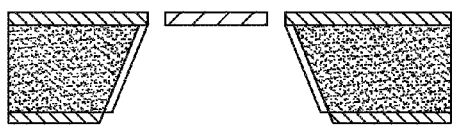
Figure 3H:
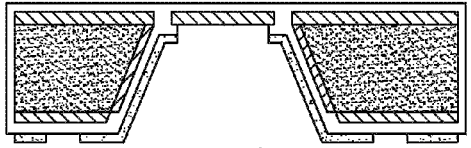
Figure 3E:
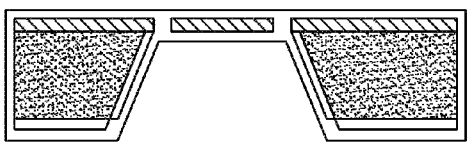
Figure 3I:
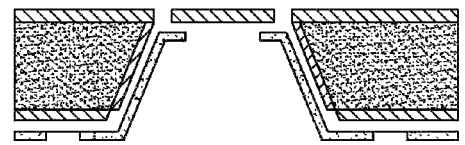

To establish electrical connectivity using backside wire bonding, reactive ion etching may be performed on the silicon nitride diaphragm, as illustrated in FIG. 3D, to generate a pair of access slits. The reactive ion etching may be performed at about 100 m Torr and at about 150 W. In the illustrated embodiment, the spacing of the slits may be about 6 micrometers in width, to allow for conformal deposition of polysilicon. As illustrated in FIG. 3E, a layer of polysilicon (which may have a thickness of about 3 μm) is conformally deposited by LPCVD, then the polysilicon layer is doped with phosphorus. As explained earlier, the doping concentration may be adjusted to adjust the resistance. In the illustrated embodiment, the doping may be performed at a concentration of about $10^{16}$/cm$^3$ at 40 KeV. The doping may be followed by annealing at about 1000° C.

The doping and annealing may be followed by aluminum metallization. sputtering of a thin film of aluminum. In FIG. 3F, the polysilicon strip on the backside, of length about 40 μm, may be etched and patterned at the center using RIE. A thin film of aluminum may then be sputtered, as shown in FIG. 3G. The aluminum layer may have a thickness of about 0.4 μm. On the backside, aluminum metallization may be patterned at three locations, as shown in FIG. 3G. On the front side, the poly-silicon layer may be patterned to form the sensing element 140, at 2 μm in width and 80 μm in length, as shown in FIG. 3H.

FIGS. 4A-4D illustrate SEM photos of the MEMS shear stress sensor. FIG. 4A illustrates the sensing element 140, formed of phosphorous-doped polysilicon, and the pair of RIE-etched slits 123, through which the sensing element 140 can be connected to the backside of the sensor. FIG. 4B illustrates the KOH-etched cavity 130 from the backside. FIG. 4C illustrates a magnified view of the cavity 130, the diaphragm 120, and the parallel slits 123 that are opened by RIE and created on the silicon nitride diaphragm 120, which in the illustrated embodiment is about 0.4 μm in thickness. FIG. 4D illustrates one of the slits 123 that allow electrical contact between the sensing element on the front side and the aluminum electrodes on the backside.

The MEMS sensor 100 operates based on heat transfer principles. The wall shear stress is linearly proportionally to the stream-wise pressure gradient. From Newtonian fluid equations, the steady shear stress is given as follows $$\tau = r/2(8\mu Q/\pi r_0^4) \quad (1)$$

where τ denotes the shear stress, $r_0$ denotes the radius of channel, μ denotes, the dynamic viscosity of fluid, and Q denotes the volume flow rate (cross-section area of the channel times velocity). In a fully developed laminar flow, the boundary layer velocity profile determines the rate of heat transfer from a heated resistive element to the surrounding fluid field. The input ohmic power P delivered to the sensing element 140, when a voltage V is applied across the sensing element 140, is defined as $$P = \frac{V^2}{R}.$$

Studies have shown that a linear relationship is obtained between $V^2$ and $\tau^{1/3}$, as follows:

$$\frac{V^2}{R} = (A_T + B_T \tau^{1/3}), \quad (2)$$

In equation (2) above, $A_T$ is an empirical coefficient, determined by a combination of effective area of the sensing element, the stream wise length of the sensing element, heat capacity, thermal conductivity, and viscosity of fluid. $B_T$ denotes the conductance heat loss to the surface and R is the resistance of the sensing element 140 at room temperature.

The resistance R is given by:

$$R = R_0[1 + \alpha(T - T_0)], \quad (3)$$

where $R_0$ is the resistance at room temperature $T_0$, and alpha, $\alpha$, is the temperature coefficient of resistance (TCR).

The resistance over heat ratio $D_R$ can be obtained as follows:

$$D_R = \frac{R - R_0}{R_0} \quad (4)$$

where R denotes the resistance at experimental temperature, and $R_0$ is the resistance at ambient temperature. The higher the resistance over heat ratio $D_R$ is, the higher the sensitivity will be. In one embodiment, the resistance over heat ratio may be set at about 0.06.

From equations (1) and (2) above, it can be seen that the desired shear stress can be obtained by measuring the change in heat convection (related to the velocity of the flowing fluid, which in turn is related to the volume flow rate Q in equation (1)). As explained earlier, the change in heat convection may be determined by measuring a change in voltage across the sensing element.

The electronic system 150 may thus be configured, in one embodiment, to measure the change in heat convection from the sensing element to the surrounding fluid by determining a change in voltage across the sensing element that is required in order to maintain the sensing element at a substantially constant temperature. The electronic system 150 may be configured to determine the shear stress from the measured change in heat convection, by finding a value of the shear stress that satisfies equation (2) above.

The operation and fabrication MEMS sensor 100 has been described above in conjunction with the measurement of fluid shear stress. It should be noted that the same techniques, principles, and equations, described above, can be used to measure vascular parameters other than shear stress, including but not limited to pressure, flow rate, and temperature.

Figure 5:
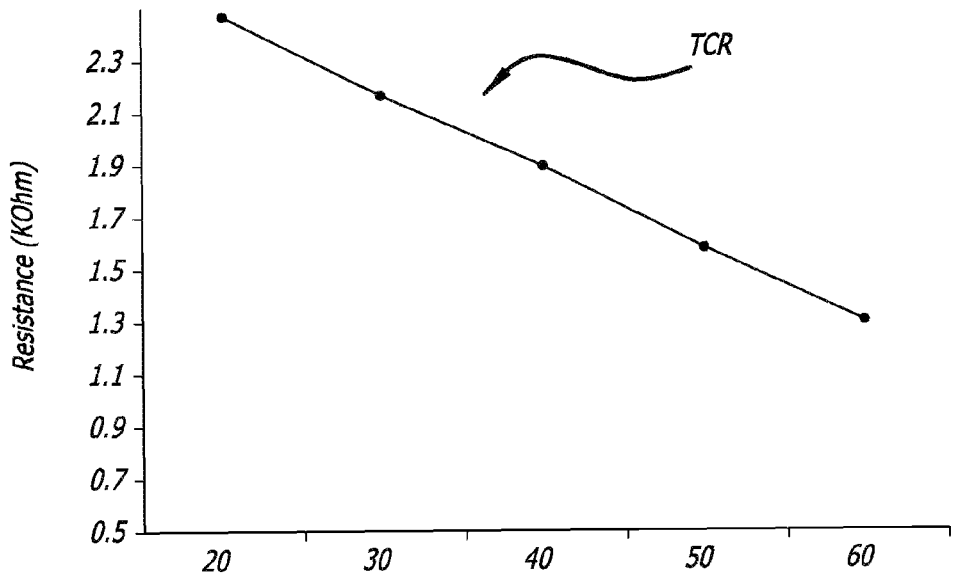
FIG. 5 illustrates a plot of the TCR for a MEMS sensor with backside wire bonding.

FIG. 5 illustrates a plot of the TCR for a MEMS sensor with backside wire bonding. FIG. 5 shows a linear relation that is established between the resistance and temperature. The resistance vs. temperature plot demonstrates a negative TCR from 20 to 60° C., suggesting a phonon scattering effect. The negative TCR is due to the phosphorus-doped polysilicon strip. In the illustrate embodiment, the absolute TCR between 20 to 40° C. may be estimated to be about 0.9937.

Figure 6:
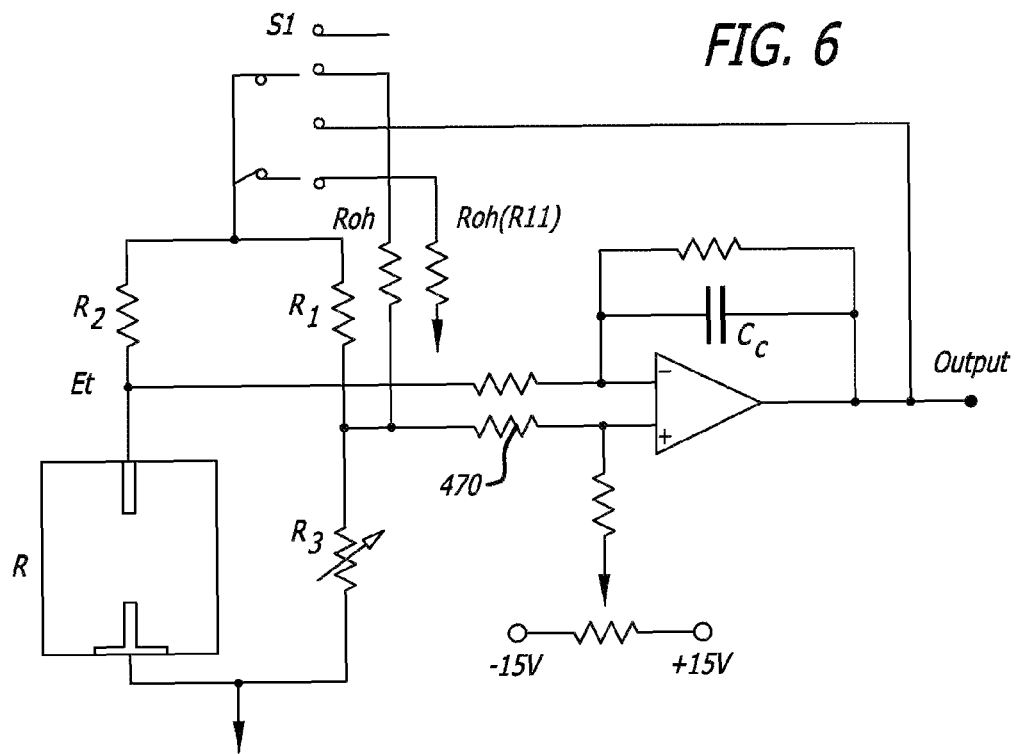
FIG. 6 illustrates an exemplary driver circuit configured to drive the MEMS sensor.

FIG. 6 illustrates an exemplary driver circuit 300 configured to drive the MEMS sensor. In the illustrated embodiment, the driver circuit 300 includes a Wheatstone bridge and a differential operation amplifier. The Wheatstone bridge network may be used for maintaining constant voltage across the bridge. A constant temperature mode circuit may be used, which has two advantages: (1) low over heat ratio of 6%, obtained from resistance over heat ratio, and (2) short response time. The value of the resistance R may be adjusted to establish a balance in the bridge by the feedback circuit. Initially, the Wheatstone bridge may be balanced between the resistors on the upper arm and the lower arm so that the input voltage difference to the operational amplifier is zero. As the fluid flows past the surface of the sensing element 140, the resistance of the sensor element changes in response, because of heat loss. The change in sensor resistance results in an imbalance in the Wheatstone bridge network. This change is reflected across the operational amplifier. A feedback circuit restores the balance in the network by voltage compensation.

Figure 7A:
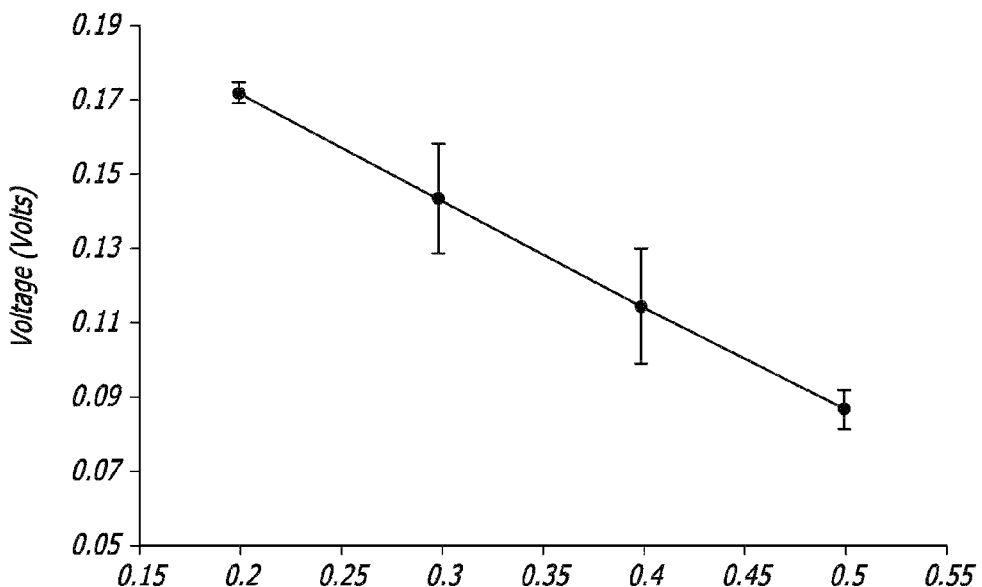
FIG. 7A illustrates a plot of the average output voltage signals and the steady flow rates.

Calibration may be conducted for the MEMS sensor 100 to establish a linear relation between $V^2$ and $\tau^{1/3}$. By plotting voltage vs. flow rates, as shown in FIG. 7A, a relation can be obtained between voltage and shear stress, using equation (2). FIG. 7A illustrates a linear relationship between the average output voltage signals and the steady flow rates, ranging from 1.0 to 5.0 ml/min. Individual steady flow rates $Q_n$ may be generated, and the voltage signals Vn may be obtained as the average output signals from the MEMS sensor, corresponding to these individual flow rates at 26±0.15° C. As shown in FIG. 7A, the voltage decreases as the temperature rises, reflecting the negative TCR of the phosphorous-doped polysilicon.

Figure 7B:
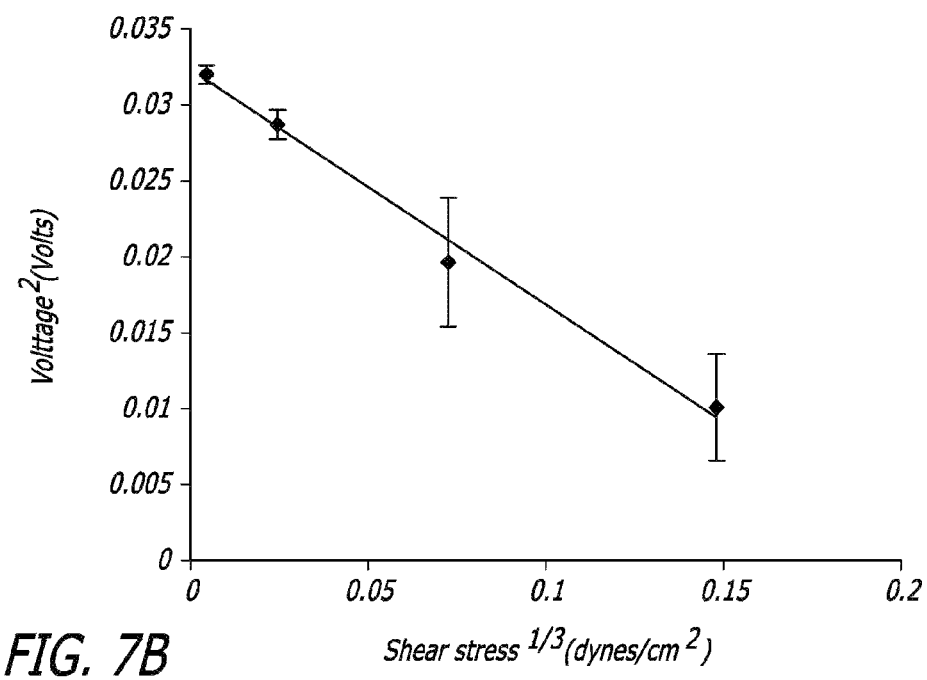
FIG. 7B illustrates a calibration curve of $V^2$ and $\tau^{1/3}$.

FIG. 7B illustrates a linear calibration between $V_2$ and $\tau^{1/3}$. The shear stress value corresponding to the 3 individual flow rates may be calculated using $\tau_w = r/2(8 \mu Q/\pi r_0^4)$ where $r_0$ is the radius of the channel, $\mu$ the dynamic viscosity of fluid, Q the flow rate of the medium, and $\pi$ is a constant. The linear relation between $V^2$ and $\tau^{1/3}$ may be obtained by plotting the averaged voltage output signals ($V_n$) with the corresponding mean shear stress. The negative slope shown in FIG. 7B reflects the effect of negative TCR as a result of the phosphorous doped polysilicon strip.

Figure 7C:
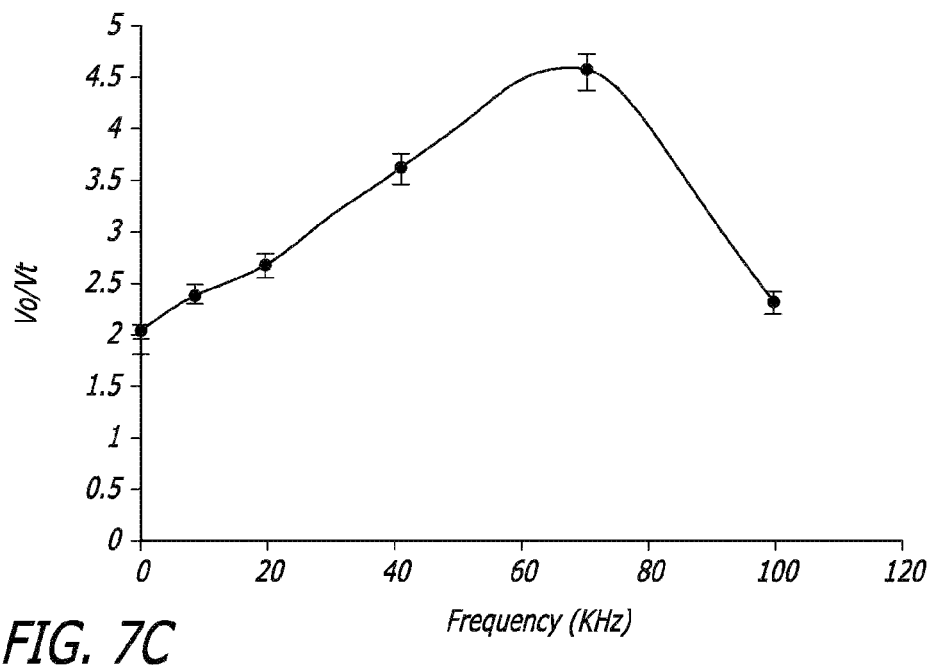
FIG. 7C illustrates a frequency response of the MEMS sensor.

FIG. 7C illustrates a frequency response of the MEMS sensor 100. The frequency response may be obtained by measuring the magnitude of the voltage gain over a range of frequency. The sine wave may be introduced through the node $E_t$ (shown in FIG. 6) of the constant temperature mode driving circuit. The gain may be measured by adjusting the amplitude of the sine wave input signal, $V_r$, using a feedback amplifier. In the embodiment illustrated in FIG. 7C, the MEMS sensor operates at a maximal gain of ~4.5 at a frequency of 71 KHz.

Figure 7D:
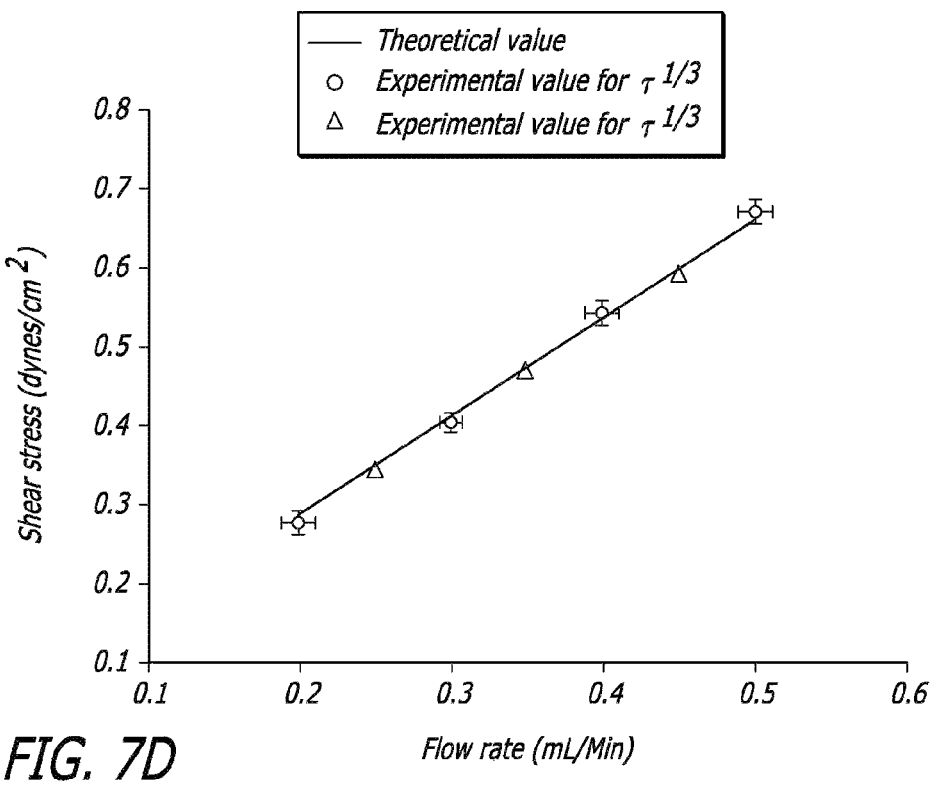
FIG. 7D compares the experimentally measured shear stress values with theoretically calculated shear stress values.

FIG. 7D compares the experimentally measured shear stress values with theoretically calculated shear stress values. As seen from FIG. 7D, the experimental values overlap with the theoretical values. In FIG. 7D, the straight line represents theoretical values, the squares denote measured values by using the calibration curve of $V^2$ versus $\tau^{1/3}$, and the triangle denotes the measured values. The Y-error bar indicates the standard deviation of the shear stress, while the X-error bar indicates the standard deviation for voltage. The experimental values are in agreement with the theoretical predictions.

In sum, improved methods and systems have been designed to obtain real-time vascular parameters in geometrically complicated arterial circulation. These parameters include, but are not limited to, shear stress, pressure, flow rate, and temperature. A number of design features are implemented with MEMS sensors for biomedical applications. Backside wire bonding is implemented, and insulation of external wire contacts are made on the backside of the device. This approach allows for precise wall shear stress measurement without flow disturbance as a result of wire bonding. The micro-circuitry is established on the backside of the sensor through the electric connection between the aluminum metallization on the backside and the phosphorous-doped polysilicon on the front side.

In addition, a KOH-etched cavity minimizes heat transfer from the sensing element to the substrate, thereby optimizing heat transfer to the fluid, and simplifying sensor fabrication steps. Thermal isolation also optimizes the sensitivity of the MEMS sensors. Further, the polysilicon sensing element is uniformly doped with phosphorous to generate a sheet resistance at 32 $\Omega/cm^2$ and a resistance value of 2.5 k$\Omega$ at room temperature. (For comparison, MEMS sensor resistances typically lie in the range of 1 to 5 k$\Omega$, and traditional metal sensors typically have resistances ranging from 5-50$\Omega$). This high resistance results in an increase in the sensor's sensitivity.

While certain embodiments have been described of systems and methods for measuring vascular parameters such as fluid shear stress, it is to be understood that the concepts implicit in these embodiments may be used in other embodiments as well. The protection of this application is limited solely to the claims that now follow.

In these claims, reference to an element in the singular is not intended to mean "one and only one" unless specifically so stated, but rather "one or more." All structural and functional equivalents to the elements of the various embodiments described throughout this disclosure that are known or later come to be known to those of ordinary skill in the art are expressly incorporated herein by reference, and are intended to be encompassed by the claims. Moreover, nothing disclosed herein is intended to be dedicated to the public, regardless of whether such disclosure is explicitly recited in the claims. No claim element is to be construed under the provisions of 35 U.S.C. §112, sixth paragraph, unless the element is expressly recited using the phrase "means for" or, in the case of a method claim, the element is recited using the phrase "step for."

What is claimed is:

1. A method of fabricating a micromachined shear stress sensor, the method comprising:
    depositing a layer of silicon nitride on a substrate and etching the substrate to form a cavity having an overlying diaphragm, the substrate having a front-side surface and a backside surface;
    performing reactive ion etching on the diaphragm to create a plurality of access slits on the diaphragm;
    conformally depositing a layer of polysilicon on the substrate, then doping the polysilicon layer with phosphorus;
    sputtering a layer of aluminum onto the backside surface of the substrate, and patterning the aluminum layer to form a plurality of electrode leads;
    patterning the polysilicon layer on the front-side surface of the substrate to form a strip of heat sensing element; and
    connecting a plurality of wire bonds between the sensing element on the front-side surface and the electrode leads on the backside surface, by passing the wire bonds through the access slits on the diaphragm.

2. The method of claim 1, further comprising annealing the doped polysilicon layer at about 1000 degrees Celsius, after the act of doping the polysilicon layer with phosphorus and before the act of sputtering the layer of aluminum.

3. The method of claim 1, further comprising the act of patterning the polysilicon layer on the backside surface of the substrate using RIE, after the act of annealing the doped polysilicon layer and before the act of sputtering the layer of aluminum.

4. The method of claim 1, further comprising the act of growing a layer of silicon dioxide by thermal oxidation at a temperature of about 1050 degrees Celsius, after the act of etching the substrate to form the cavity and before the act of performing reactive ion etching on the diaphragm.

5. The method of claim 1, wherein the act of depositing the layer of silicon nitride comprises uniformly depositing the layer of silicon nitride by LPCVD.

6. The method of claim 1, wherein the act of etching the substrate to form the cavity comprises performing anisotropical wet-etching by KOH.

* * * * *